(12) United States Patent  (10) Patent No.: US 9,121,838 B2
Farooq et al.  (45) Date of Patent: Sep. 1, 2015

(54) AMMONIA SENSOR USING WAVELENGTH MODULATION SPECTROSCOPY

(71) Applicant: King Abdullah University of Science and Technology, Thuwal (SA)

(72) Inventors: Aamir Farooq, Thuwal (SA); Kyle Owen, Lompoc, CA (US)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 6 days.

(21) Appl. No.: 14/189,293

(22) Filed: Feb. 25, 2014

(65) Prior Publication Data

US 2014/0293283 A1  Oct. 2, 2014

Related U.S. Application Data

(60) Provisional application No. 61/768,804, filed on Feb. 25, 2013.

(51) Int. Cl.
*G01N 21/00* (2006.01)
*G01N 33/00* (2006.01)
*G01N 21/61* (2006.01)

(52) U.S. Cl.
CPC ............ *G01N 33/0054* (2013.01); *G01N 21/61* (2013.01)

(58) Field of Classification Search
CPC . G01N 21/39; G01N 21/3504; G01N 21/031; G01N 2021/399; G01J 3/42
USPC .......................................................... 356/437
See application file for complete search history.

(56) References Cited

U.S. PATENT DOCUMENTS

2006/0217626 A1* 9/2006 Patel et al. .................... 600/532
2013/0256227 A1* 10/2013 Kelly et al. .................... 210/638

* cited by examiner

*Primary Examiner* — Tari Fur Chowdhury
*Assistant Examiner* — MD Rahman
(74) *Attorney, Agent, or Firm* — Steptoe & Johnson LLP

(57) ABSTRACT

An ammonia sensor can include a laser detector configured to provide stable sample readings. The sensor can implement a method including processing the recorded intensity of the laser beam to determine a first harmonic component and a second harmonic component and the amount of ammonia in the sample.

36 Claims, 17 Drawing Sheets

(a) Measurement of 7.3 ±2.1 ppb.

(b) Measurement of 18.3 ±3.3 ppb.

(c) Measurement of 154.6 ±3.3 ppb.

AMMONIA SENSOR USING WAVELENGTH MODULATION SPECTROSCOPY

CROSS-REFERENCE TO RELATED APPLICATION

This application claims priority to U.S. Provisional Patent Application No. 61/768,804 filed on Feb. 25, 2013, the entire contents of which are specifically incorporated by reference herein without disclaimer.

BACKGROUND

A gas sensor is a device that detects the presence of gases. Gas sensors can be used for various industries, including medical care. Gas sensors can be portable, hand-held instruments as well as fixed detectors that can be stationed in buildings, field sites or stations. In addition to sensing the existence of gases, a gas sensor can measure the concentration of gases using absorption spectroscopy.

SUMMARY

In general, wavelength modulation spectroscopy with second harmonic normalized by first harmonic detection (WMS 2f/1f) can be used to develop gas sensors. A gas sensor that detects ammonia can be used to diagnose and monitor many diseases, including chronic kidney disease.

In one aspect, a method of detecting the amount of ammonia in a sample can include flowing a gas including ammonia from a subject through a multi-pass absorption cell, passing a laser beam through the gas in the multi-pass absorption cell, detecting the intensity of the laser beam after the laser beam passes through the gas in the multi-pass absorption cell, recording the intensity of the laser beam after the intensity of the laser beam is detected, and processing the recorded intensity of the laser beam to determine a first harmonic component and a second harmonic component and the amount of ammonia in the sample.

In some embodiments, the gas flow can be continuous.

In some embodiments, the laser beam intensity can be filtered with a filter to remove high frequency noise and to isolate the first and the second harmonics. In some embodiments, the second harmonic can be normalized by the first harmonic. In some embodiments, a low frequency modulation can be added to a high frequency modulation to determine a second harmonic normalized by a first harmonic for a range of wavelengths. In some embodiments, peak of the second harmonic normalized by the first harmonic can be determined. In some embodiments, a background signal can be measured. In some embodiments, the background signal can be subtracted from the second harmonic normalized by the first harmonic. In some embodiments, an ammonia mole fraction can be determined using a background subtracted second harmonic normalized by the first harmonic. In some embodiments, the ammonia mole fraction can be determined using Beer's Law.

In some embodiments, the multi-pass absorption cell can be pretreated with the gas to reach an equilibrium.

In some embodiments, the amount of ammonia can be detected to diagnose or monitor chronic kidney disease. In some embodiments, the amount of ammonia can be detected during dialysis. In some embodiments, the amount of ammonia can be detected to diagnose or monitor *helicobacter pylori* infection. In some embodiments, the amount of ammonia can be detected to diagnose or monitor encephalopathy. In some embodiments, the amount of ammonia can be detected to diagnose or monitor chronic liver disease.

In another aspect, a method of diagnosing or monitoring chronic kidney disease can include flowing a gas including ammonia from a subject through a multi-pass absorption cell, passing a laser beam through the gas in the multi-pass absorption cell, detecting the intensity of the laser beam after the laser beam passes through the gas in the multi-pass absorption cell, recording the intensity of the laser beam after the intensity of the laser beam is detected, and processing the recorded intensity of the laser beam to determine a first harmonic component and a second harmonic component and the amount of ammonia in the sample.

In another aspect, a sensor for detecting ammonia can include a sample reservoir configured to contain a gas including ammonia from a subject, a first controller configured to adjust pressure and flow rate of the gas from the sample reservoir into a first conduit, a multi-pass absorption cell fluidly connected to the first conduit and configured to contain a portion of the gas from the sample reservoir, a laser source configured to pass a laser beam through the gas in the multi-pass absorption cell, a detector configured to measure the intensity of the laser beam, and an analyzer configured to provide a concentration of ammonia in the gas.

In some embodiments, a cooling system can be configured to cool the laser source. In some embodiments, the sensor can include collimation optics between the laser source and the multi-pass absorption cell. In some embodiments, a recorder can be configured to record the laser beam intensity after the laser beam passes through the gas in the multi-pass absorption cell.

In some embodiments, a first pressure measuring instrument can be configured to measure the pressure of the gas, wherein the pressure measuring instrument can be between the sample reservoir and the multi-pass absorption cell. In some embodiments, the sensor can be calibration free. In some embodiments, the sample reservoir can include breath sample. In some embodiments, the first controller can be configured to keep the pressure substantially constant.

In some embodiments, the laser source can include a quantum cascade laser. In some embodiments, the laser source can be tunable over 1100.4 to 1108.2 $cm^{-1}$. In some embodiments, the laser source can be configured to operate near 1103.46 $cm^{-1}$.

In some embodiments, the multi-pass cell further can include a gas outlet connecting to a second controller configured to adjust pressure and flow rate of the gas from the multi-pass absorption cell into a second conduit. In some embodiments, the second controller can be configured to connect to a vacuum pump through the second conduit. In some embodiments, the sensor can include a second pressure measuring instrument configured to measure the pressure of the gas, wherein the pressure measuring instrument can be between the gas outlet and the vacuum pump.

In some embodiments, the pressure of the multi-pass cell can be less than 200 Torr. In some embodiments, the ammonia detected can be between 10 parts-per-billion to 5 parts-per-million.

In some embodiments, the sensor can be portable.

In some embodiments, the uncertainty of the sensor can be less than 10%. In some embodiments, the uncertainty of the sensor can be less than 7%. In some embodiments, the uncertainty of the sensor can be less than 5%. In some embodiments, the uncertainty of the sensor can take into account interference, spectroscopic parameters, laser parameters, path length, and pressure.

Other aspects, embodiments, and features will be apparent from the following description, the drawings, and the claims.

DETAILED DESCRIPTION

Figure 1:
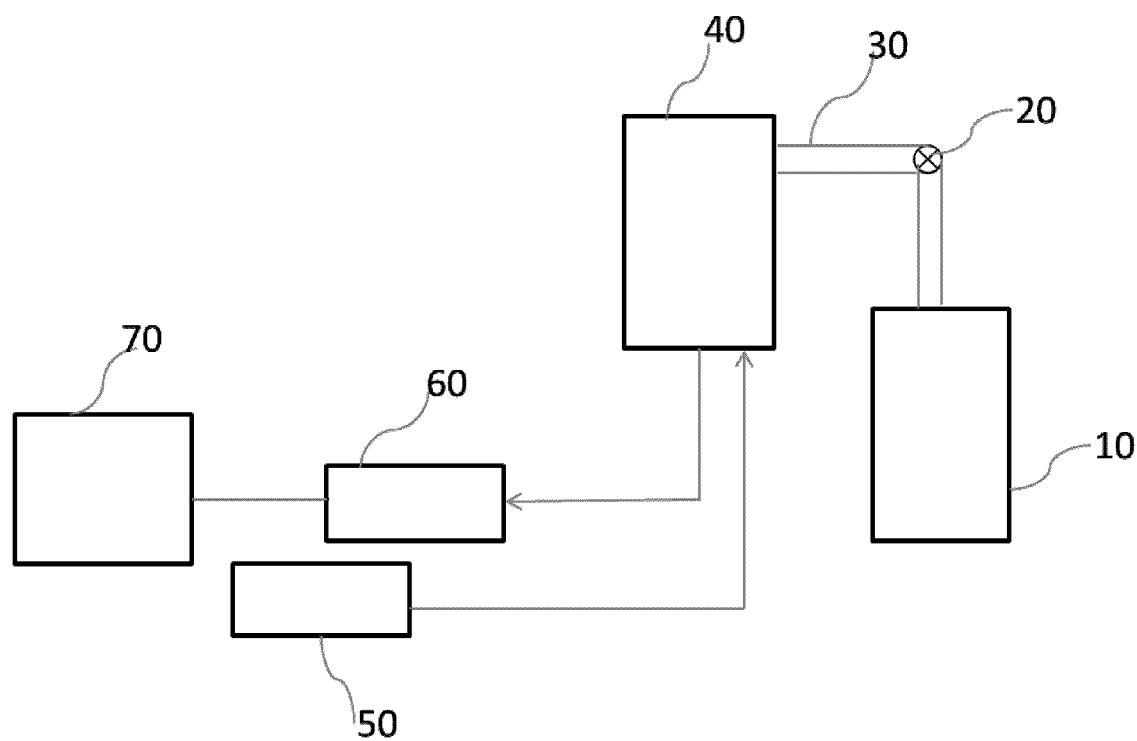
FIG. 1 is a schematic drawing of a sensor.

The development of accurate, reliable gas sensors has the potential to be used in many fields, including medical care. Wavelength modulation spectroscopy with second harmonic normalized by first harmonic detection (WMS 2f/1f) is a sensitive technique and can be used in the development of gas sensors, including calibration-free sensors. A gas sensor can operate when there is a continuous gas flow. FIG. 1 is a schematic drawing of a gas sensor. In FIG. 1, a sample reservoir 10 can contain a gas including ammonia from a subject; a controller 20 can be configured to adjust pressure and flow rate of the gas from the sample reservoir into a first conduit 30; a multi-pass absorption cell 40 can be connected to the first conduit 30 and configured to contain a portion of the gas from the sample reservoir 10; a laser source 50 can be configured to pass a laser beam through the gas in the multi-pass absorption cell 40, a detector 60 can be configured to measure the intensity of the laser beam, and an analyzer 70 can be configured to provide a concentration of a gas, such ammonia.

To detect a gas and its concentration, such as ammonia and the concentration of ammonia, a method can include flowing a gas, such as a gas including ammonia, from a subject through a multi-pass absorption cell, passing a laser beam through the gas in the multi-pass absorption cell, detecting the intensity of the laser beam after the laser beam passes through the gas in the multi-pass absorption cell, recording the intensity of the laser beam after the intensity of the laser beam is detected, and processing the recorded intensity of the laser beam to determine a first harmonic component and a second harmonic component.

An ammonia gas sensor using a quantum cascade laser operating near 1103 cm$^{-1}$ and a multi-pass cell can be developed with a 10 ppb detectability limit and 6% total uncertainty for breath measurements. The sensor can be used to detect ammonia in exhaled breath and to compare healthy patients to ill patients, such as patients diagnosed with chronic kidney disease (CKD).

A gas sensor, a gas detector or a gas monitoring system, is a device that detects the presence of various gases. Gas sensors can be used for various industries including medicine, mining, police, fire, rescue, shipping, transportation, telecom, oil and gas industries. Gas sensors include portable, handheld instruments as well as fixed detectors that can be stationed in buildings, field sites or stations. Gas sensors provide personnel with early warning of poisonous gases such as $H_2S$, CO, $O_2$, $SO_2$, $PH_3$, $NH_3$, $NO_2$, HCN, $Cl_2$, $ClO_2$, $O_3$, volatile organic compounds, and combustibles. Gas sensor can incorporate audible alarms, visual warning lights, vibrate alarms, wireless digital transmitters, and solar-powered systems.

In addition to sensing the existence of gases, the concentration of gases can be measured. One of the methods is direct absorption spectroscopy, provide quantitative assessments of species. This technique can include of a tunable laser source, sample cell and detector. If a gaseous absorber is present inside the cell, the transmitted throughput power will have a gap at the absorption wavelength, the amplitude of which is directly proportional to the specious concentration and can be calculated.

One disadvantage of direct absorption spectrometry is that it relies on a measurement of a small change in power from a high level; any noise introduced by the light source or the transmission through the optical system will deteriorate the sensitivity of the technique.

To reach higher sensitivity, modulation technique can be included. Wavelength modulation spectroscopy (WMS) is a form of optical absorption spectroscopy that allows detection of small optical absorbances of gases and, thereby, measurements of gas concentrations. It provides advantages over direct absorption spectroscopy. One advantage is that it measures a difference signal which is directly proportional to the species concentration. Another advantage is that it makes use of the fact that technical noise usually decreases with increasing frequency and improves on the signal contrast by encoding and detecting the absorption signal at a high frequency, where the noise level is low. WMS allows shifting a measured signal to a higher frequency region, thereby offering a larger signal-to-noise ratio and thus higher sensitivity.

FIG. 1 is a schematic drawing of a sensor using WMS. A sample reservoir 10 can contain a gas including ammonia from a subject; a controller 20 can be configured to adjust pressure and flow rate of the gas from the sample reservoir into a first conduit 30; a multi-pass absorption cell 40 can be connected to the first conduit 30 and configured to contain a portion of the gas from the sample reservoir 10; a laser source 50 can be configured to pass a laser beam through the gas in the multi-pass absorption cell 40, a detector 60 can be configured to measure the intensity of the laser beam, and an analyzer 70 can be configured to provide a concentration of a gas, such ammonia.

Laser-based sensors can be used to determine the mole fraction of species of interest in a gas mixture using absorption spectroscopy, which is governed by Beer's Law, $$\frac{I}{I_o} = \exp(-\alpha_v)$$

which relates the intensity transmitted through a gas medium, $l$, to the incident intensity, $I_o$, by the absorbance, $\alpha_v$, which is a function of the laser path length, L, the total pressure of the gas, P, the mole fraction of the absorbing species, X, and spectroscopic parameters that make up the linestrength, S, and lineshape, $\phi_v$.

$$\alpha_v = SPXL\phi_v$$

The incident and transmitted intensity are measured which enables the determination of the mole fraction if the other parameters are known. Spectroscopic parameters that define the linestrength and lineshape can determine the mole fraction when the pressure and path length are known. This method is challenging for accurate detection of trace gases since the low absorbance due to low concentrations leads to a small signal-to-noise ratio (SNR).

An improvement in the SNR can be obtained through the use of WMS. In order to develop a calibration-free sensor, WMS 2f/1f can be used. See, for example, Rieker, G. B., et al., *Appl Opt* 2009, 48, 5546-60, which is incorporated by reference in its entirety. WMS is employed by modulating the laser wavelength sinusoidally at a high frequency. As the wavelength is modulated, the intensity is modulated as well. The first and second harmonic components of the transmitted intensity are extracted from the measured raw signal. The ratio of the second harmonic signal to the first harmonic signal is a function of the laser parameters, spectroscopic parameters (S, $\phi_v$), and gas parameters (P, T, L, and X). The laser parameters can be determined before the measurements. See, for example, Li, H., et al., *Appl Opt* 2006, 45, 1052-61, which is incorporated by reference in its entirety. Therefore, the sensor can be used to measure the mole fraction of gases, such as ammonia. This strategy is called "calibration-free" because it allows for the measurement of mole fraction without the need to calibrate the signal to a known mixture, as is necessary with traditional WMS and other gas sensing techniques. See, for example, Rieker, G. B., et al., *Appl Opt* 2009, 48, 5546-60, which is incorporated by reference in its entirety.

The amount of ammonia in exhaled breath has been linked to a variety of adverse medical conditions, including Chronic Kidney Disease (CKD). For healthy individuals, ammonia is present in exhaled breath at typical levels of a few hundred parts per billion (ppb). Research has linked CKD to elevated levels, greater than one parts per million (ppm). See, for example, Manne, J., et al., *Applied Optics* 2006, 45, 9230-9237, which is incorporated by reference in its entirety. A method of detecting the amount of ammonia in a sample to diagnose or monitor chronic kidney disease can include flowing a gas including ammonia from a subject through a multi-pass absorption cell, passing a laser beam through the gas in the multi-pass absorption cell, detecting the intensity of the laser beam after the laser beam passes through the gas in the multi-pass absorption cell, recording the intensity of the laser beam after the intensity of the laser beam is detected, and processing the recorded intensity of the laser beam to determine a first harmonic component and a second harmonic component and the amount of ammonia in the sample. The gas flow can be continuous.

In addition to the diagnosis and monitoring of CKD, ammonia breath sensors have been used during dialysis to monitor the treatment of CKD. In addition, the ammonia levels can be measured in breath of patients undergoing hemodialysis who had CKD. Before dialysis, the ammonia levels can be between 1.5 and 2.0 ppm. The levels can drop sharply during the treatment and eventually can reach levels between 150 and 200 ppb. The breath measurements can be compared to blood tests, correlating the breath levels to Blood Urea Nitrogen (BUN) and Creatinine. Breath measurements have an advantage over blood tests in that they can be performed more frequently as well as during the treatment. Currently, blood tests are generally done once a month and blood is generally only taken before and after the treatment. Breath ammonia measurements can improve the quality of renal care by providing a fast, painless, cost-effective in situ monitor to measure dialysis progress in real time. See, for example, Narasimhan, L. R., et al., *Proceedings of the National Academy of Sciences of the United States of America* 2001, 98, 4617-4621, which is incorporated by reference in its entirety. A method of detecting the amount of ammonia in a sample during dialysis can include flowing a gas including ammonia from a subject through a multi-pass absorption cell, passing a laser beam through the gas in the multi-pass absorption cell, detecting the intensity of the laser beam after the laser beam passes through the gas in the multi-pass absorption cell, recording the intensity of the laser beam after the intensity of the laser beam is detected, and processing the recorded intensity of the laser beam to determine a first harmonic component and a second harmonic component and the amount of ammonia in the sample.

Breath ammonia measurements may also be a feasible diagnostic test for the *Helicobacter Pylori* Infection. Subjects who tested positive for *Helicobacter Pylori* can respond differently than subjects who tested negative for *Helicobacter Pylori*. Ammonia levels in breath can be recorded while subjects breathed normally; the patients then can ingest a Urea tablet and continued breathing. Positive subjects can show a rapid rise in ammonia during baseline and minimal change after taking the tablet, while negative subjects can show a rise in ammonia after taking the tablet. See, for example, Kearney, D. J., et al., *Digestive Diseases and Sciences* 2002, 47, 2523-2530, which is incorporated by reference in its entirety. A method of detecting the amount of ammonia in a sample to diagnose or monitor *helicobacter pylori* infection can include flowing a gas including ammonia from a subject through a multi-pass absorption cell, passing a laser beam through the gas in the multi-pass absorption cell, detecting the intensity of the laser beam after the laser beam passes through the gas in the multi-pass absorption cell, recording the intensity of the laser beam after the intensity of the laser beam is detected, and processing the recorded intensity of the laser beam to determine a first harmonic component and a second harmonic component and the amount of ammonia in the sample.

Breath ammonia measurements can also have clinical significance for the diagnosis of encephalopathy associated with hyperammonemia. Patients with chronic liver disease can have elevated breath ammonia levels when their blood ammonia concentrations can increase above 90 µg/dl; the normal range is between 12-66 µg/dl. Patients who have relatively higher breath ammonia concentration when compared to blood ammonia concentration can be found to have subclinical encephalopathy. See, for example, Wakabayashi, H., et al., *Metabolic Brain Disease* 1997, 12, 161-169, which is incorporated by reference in its entirety. A method of detecting the amount of ammonia in a sample to diagnose or monitor chronic liver disease can include flowing a gas including ammonia from a subject through a multi-pass absorption cell, passing a laser beam through the gas in the multi-pass absorption cell, detecting the intensity of the laser beam after the laser beam passes through the gas in the multi-pass absorption cell recording the intensity of the laser beam after the intensity of the laser beam is detected, and processing the recorded intensity of the laser beam to determine a first harmonic component and a second harmonic component and the amount of ammonia in the sample.

Based on the established link between ammonia breath concentration and adverse medical conditions, the development of accurate sensors can improve medical treatment. Laser-based sensors show great potential as they can achieve high sensitivity, provide real-time analysis, and their size makes them portable. A laser-based ammonia sensor can be designed to achieve improved sensitivity.

Breath samples can be collected to detect the amount of ammonia. One method of breath analysis can include real time collection of breath sample. For example, to collect and analyze breath sample in real time, the breath of a test subject, such as a patient, can be connected to a sample reservoir that can produce a flow rate and pressure for a gas sensor. The flow rate and pressure can be substantially constant. Breath sample can also be collected in gas sampling bags, in evacuated canisters, or on thermal adsorbents. When collecting breath sample with a sampling bag, a patient can exhale into the sample bag through a fitting and then close the sample bag. A breath sample bag can also be used for real time measurement. For example, soon after breath is collected in a breath sample bag, the sample bag can release breath gas to a sample reservoir that can produce a flow rate and pressure for a gas sensor. The flow rate and pressure can be substantially constant. The sample reservoir can be evacuated before the sample bag releases breath gas to the sample reservoir.

A multi-pass absorption cell can be used to improve detection sensitivity by increasing the total optical path length that travels through a small, constant sample volume. When testing a multi-pass cell for use with ammonia, the measured amount of ammonia in the cell can decrease over time because ammonia gas tends to adsorb to surfaces it comes in contact with. Due to this phenomenon, the cell is preferred not to be used to study a static gas sample. Instead, a gas flow setup is preferred so the sensor measures the actual amount of ammonia in the gas sample. Since the goal of this sensor is to measure the mole fraction of ammonia in a gas sample, and adsorption is a process which changes the amount of ammonia in the gas phase, adsorption effects need to be reduced.

Adsorption is an equilibrium process; the position of the equilibrium depends on three factors: the pressure, the temperature, and the stability of the molecule. At low pressures, the fraction of surface sites occupied increases with pressure, while at high pressures it is independent of pressure. The temperature of the surface and the type of gas can also change the equilibrium constant, since it depends on the heat of adsorption. The fraction of surface sites occupied at equilibrium decreases as temperature increases. The equilibrium also depends on the molecule and surface which are interacting, since the relative stability of the molecule in the adsorbed and gas phase will affect the equilibrium constant.

In the case of a flow experiment, the adsorbed molecules can be replaced by new molecules entering the cell and molecules that desorb are carried out by the flow. Therefore, after a period to reach saturation, equilibrium conditions can be reached and the effective adsorption rate decreases rapidly. For the adsorption effect to be negligible, it is necessary to have a flow that is high enough for the equilibrium to be reached on a time scale shorter than the gas-exchange time. Reliable measurements can, therefore, preferably be performed under continuous flow conditions after the equilibrium is reached. The period to reach equilibrium can be reduced by increasing the flow rate or by increasing the temperature of the surface and the gas, which shifts the equilibrium to the side of desorption. For a sensor, the flow rate can be limited by the cell volume, desired measurement pressure, and limited volume of the breath sample. Conditions can be chosen carefully to reach equilibrium at the desired pressure and flow rate in the time available.

A method of detecting the amount of a gas, such as a gas including ammonia, can include a pretreating step. The pretreating step can include a gas flowing through a cell, such as a multi-pass absorption cell, until the rate or amount of molecules that adsorb to the surface of the cell substantially equals the rate or amount of molecules that desorb from the surface of the cell. After the pretreating step, a substantially constant flow rate of the gas can produce a substantially constant measurement result of the ammonia concentration.

Sensors to measure ammonia concentration have been developed. Table 1 summarizes several laser based ammonia breath sensors. An ammonia sensor using a $CO_2$ laser operating at discrete wavelengths using an optoacoustic cell can be used to study the link between breath ammonia and CKD. See, for example, Narasimhan, L. R., et al., *Proceedings of the National Academy of Sciences of the United States of America* 2001, 98, 4617-4621, which is incorporated by reference in its entirety.

An ammonia sensor can be designed using a Quantum Cascade Laser (QCL) with quartz-enhanced photoacoustic spectroscopy (QEPAS) at the ammonia absorption near 1046.4 $cm^{-1}$. See, for example, Bakhirkin, Y., et al., *Laser Applications to Chemical, Security and Environmental Analysis* 2008, which is incorporated by reference in its entirety. Another ammonia sensor to study breath can be designed with a QCL at 967.35 $cm^{-1}$ using pulsed cavity ring-down spectroscopy (CRDS). See, for example, Manne, J., et al., *Applied Optics* 2006, 45, 9230-9237, which is incorporated by reference in its entirety. A sensor at the same wavelength using intra and inter pulse techniques with a long path length herriot cell can be designed as well. See, for example, Manne, J., et al., *Quantum Sensing and Nanophotonic Devices V* 2008, 6900, 90014-90014, which is incorporated by reference in its entirety. Another ammonia breath sensor, utilizing the 967.35 $cm^{-1}$ ammonia absorption peak, can be developed based on Quartz Enhanced Photo-accoustic Spectroscopy (QEPAS) and using a second harmonic wavelength modulation technique. See, for example, Lewicki, R., et al., *Quantum Sensing and Nanophotonic Devices Viii* 2011, 7945, which is incorporated by reference in its entirety.

In another method, an ammonia sensor can be designed at 1103.46 cm$^{-1}$. This approach can improve over other approaches because it utilizes an ammonia absorption feature with less interference than the features used for previous sensors. Carbon dioxide and water vapor, typically found in exhaled breath as 5% and 6% of the total gas mixture, respectively, also absorb laser radiation in this wavelength region. The absorption feature near 1103.46 cm$^{-1}$ has the least interference from carbon dioxide and water vapor, less than 1%.

Figure 2:
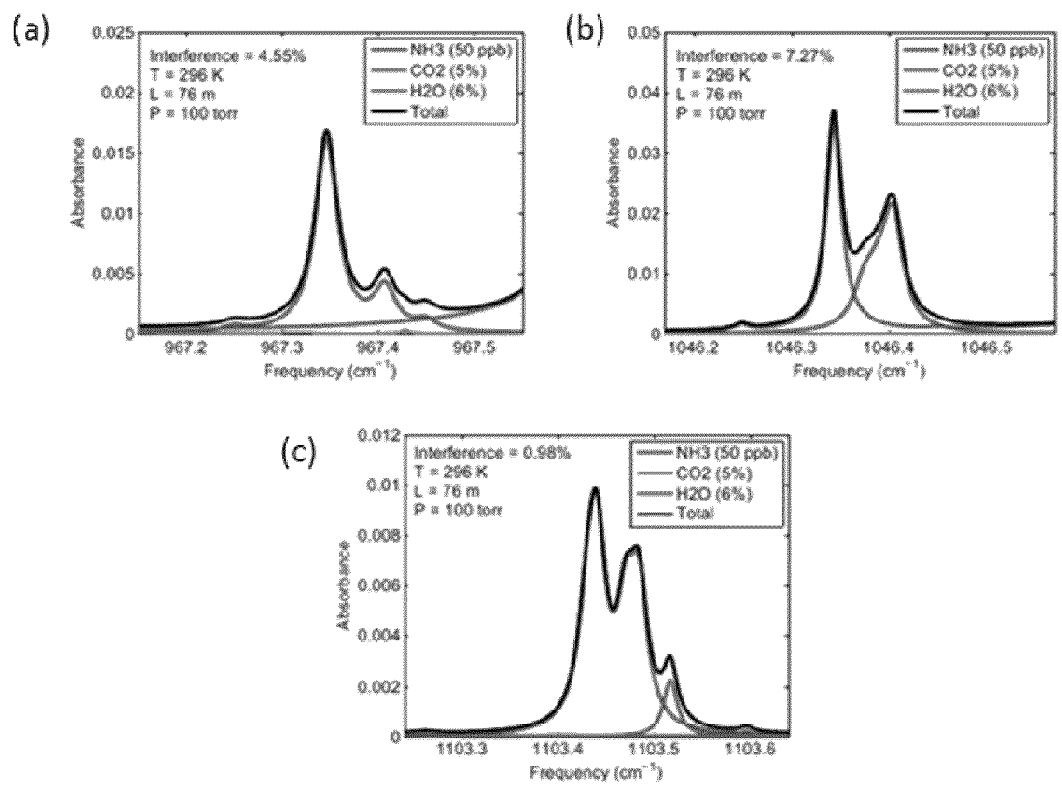
FIG. 2(a) depicts simulations of interference from carbon dioxide (5%) and water vapor (6%) on low levels of ammonia for sensor that uses ammonia feature centered at 967.35 cm$^{-1}$.
FIG. 2(b) depicts simulations of interference from carbon dioxide (5%) and water vapor (6%) on low levels of ammonia for sensor that uses ammonia feature centered at 1046.4 cm$^{-1}$.
FIG. 2(c) depicts simulations of interference from carbon dioxide (5%) and water vapor (6%) on low levels of ammonia for sensor that uses ammonia feature centered at 1103.46 cm$^{-1}$.

FIG. 2 depicts simulations of the interference from carbon dioxide (5%) and water vapor (6%) on low levels of ammonia (50 ppb) based on the high-resolution transmission molecular absorption database are used to compare ammonia features used for previous sensors to the feature selected for this sensor. See, for example, Rothman, L. S., et al., *Journal of Quantitative Spectroscopy & Radiative Transfer* 2005, 96, 139-204, which is incorporated by reference in its entirety. FIG. 2 shows a comparison between three ammonia absorption features and the interference from carbon dioxide and water vapor. The absorption centered at 1103.46 cm$^{-1}$ has less than 1% interference, the least of the four, and therefore, is an excellent candidate for an accurate, low concentration ammonia gas sensor. The sensor using 1103.46 cm$^{-1}$ thus can have strong potential in the biomedical and medical instruments industries. The sensor using 1103.46 cm$^{-1}$ can also be portable. The portability, non-intrusiveness, accuracy, and small cost of the sensor using 1103.46 cm$^{-1}$ make it very attractive for disease detection and monitoring using exhaled breath.

In addition, the detection limit for the sensor using 1103.46 cm$^{-1}$ can be less than 15 ppb; the detection limit for the sensor using 1103.46 cm$^{-1}$ can be less than 10 ppb. Although the detection limit of the sensor by Manne, J., et al., *Quantum Sensing and Nanophotonic Devices V* 2008, 6900, 90014-90014, and the detection limit of the sensor by Lewicki, R., et al., *Quantum Sensing and Nanophotonic Devices Viii* 2011, 7945, were reported to be less than 10 ppb, they were measured in nitrogen, and did not take into account the interference of carbon dioxide and water. Therefore, the sensor using 1103.46 cm$^{-1}$ has sensitivity and detectability limits that are improved over other previously designed sensors.

TABLE 1

Summary of recent laser-based ammonia breath sensors and the sensor using a detection wavelength of 1103.46 cm$^{-1}$.

| Wavelength | Laser | Method | Reported Sensitivity | Reference |
|---|---|---|---|---|
| Discrete lines in 9-10 μm | CO$_2$ | Photo-accoustic Spectroscopy (PAS) | 10% for breath measurements as low as 100 ppb | Narasimhan, L. R., et al., *Proceedings of the National Academy of Sciences of the United States of America* 2001, 98, 4617-4621. |
| 967.35 cm$^{-1}$ | QCL | Pulsed CRDS | 50 ppb detection limit | Manne, J., et al., *Applied Optics* 2006, 45, 9230-9237. |
| 1046.4 cm$^{-1}$ | QCL | QEPAS | 20 ppb standard deviation | Bakhirkin, Y., et al., *Laser Applications to Chemical, Security and Environmental Analysis* 2008. |
| 967.35 cm$^{-1}$ | QCL | Inter and Intra Pulse | 3 ppb detection limit 5% for breath measurements as low as 140 ppb | Manne, J., et al., *Quantum Sensing and Nanophotonic Devices V* 2008, 6900, 90014-90014. |
| 967.35 cm$^{-1}$ | QCL | QEPAS with WMS 2f | 6 ppb standard deviation for NH$_3$ in N$_2$ from 160 ppb to 5 ppm | Lewicki, R., et al., *Quantum Sensing and Nanophotonic Devices Viii* 2011, 7945. |
| 1103.46 cm$^{-1}$ | QCL | Multi-pass cell with WMS 2f/1f | 10 ppb detection limit Less than 6% total uncertainty for breath measurements | Device described in this application. |

Wavelength modulation spectroscopy with second harmonic normalized by first harmonic detection (WMS 2f/1f) is a sensitive technique that can be used in the development of calibration-free sensors. Laser based sensors have been developed previously with this strategy but this is the first application of this strategy to the sensitive detection of ammonia in exhaled breath. An ammonia sensor based on wavelength modulation spectroscopy with second harmonic normalized by first harmonic detection can detect ammonia when the ammonia concentration is less than 10 ppm and greater than 10 ppb. In certain embodiments, the ammonia sensor can detect ammonia when the ammonia concentration is less than 5 ppm.

EXAMPLES

Sensor Experimental Setup

Figure 3:
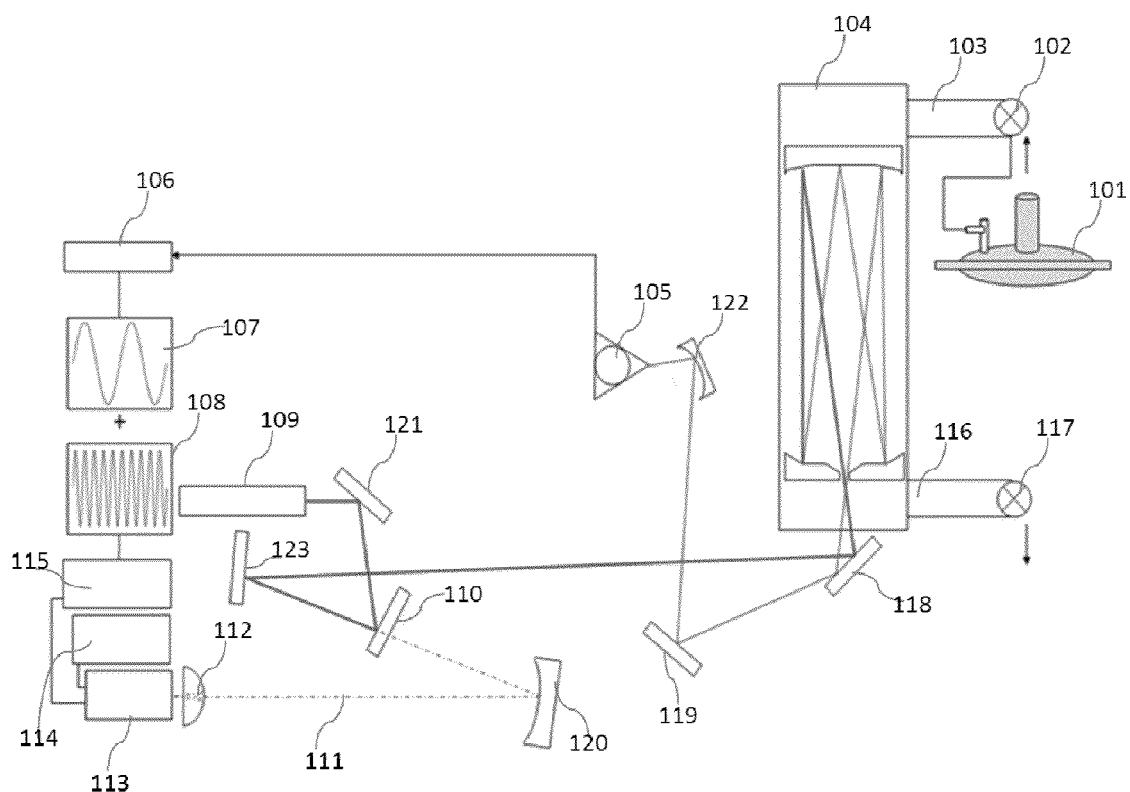
FIG. 3 depicts sensor experimental setup for Wavelength modulation spectroscopy (WMS) with a multi-pass cell.

The experimental setup is shown in FIG. 3. In FIG. 3, 101 can be a breath sample, and the sample can contain NH$_3$ in SKC exhaled breath sample bag; 102 can be a valve or controller, such as a needle valve to control pressure and flow rate; 103 can be a gas inlet; 104 can be a multi-pass absorption cell, such as an Aerodyne astigmatic multi-pass absorption cell with 238 passes totaling 76.45 meter path length; 105 can be a detector, such as a vigo detector PVI 3TE-10.6; 106 can be a data acquisition system; 107 can be a means for low frequency scan; 108 can be a means for high frequency modulation; 109 can be a laser, such as a HeNe visible laser; 110 can be a beam splitter, such as a ZnSe beam splitter; 111 can be a laser beam, such as an infrared laser beam; 112 can be an asphere, such as a ZnSe asphere; 113 can be a laser, such as an Aples Quantum Cascade Laser sbcw 2006; 114 can be a temperature controller; 115 can be a current source, such as a ILX light wave current source; 116 can be a gas outlet; 117 can be a valve or controller, such as a needle valve to control pressure and flow rate; 117 can be connected to a pressure measuring instrument, such as a pressure transducer, and to a vacuum pump; and 118 to 123 can be optics, such as optical mirrors to steer a laser beam.

A Quantum Cascade Laser (QCL) model sbcw2006 from Alpes Lasers (Neuchatel, Switzerland) was chosen since it is tunable over 1100.4 to 1108.2 $cm^{-1}$ by adjusting the laser temperature and injection current. The laser temperature was varied using the TCU200 temperature controller supplied by Alpes Lasers while the current was controlled using the ILX Lightwave LDX 3232 high compliance laser diode driver. The QCL was mounted in a laboratory laser housing which included a thermoelectric cooler. Low absorbance levels were increased by using the AMAC-76 astigmatic multi-pass cell from Aerodyne Research. See, for example, McManus, J. B., et al., *Appl Opt* 1995, 34, 3336-48; McManus, J. B., et al., *Appl Opt* 2011, 50, A74-85, each of which is incorporated by reference in its entirety. This optical cell has 238 passes leading to a total path length of 76.45 m. A ZnSe asphere was used to collimate the laser and optics were used to focus the laser at the center of the cell with a focal ratio greater than f/80 in order to achieve optimal alignment. The laser was then directed to the Vigo PVI 3TE-10.6 thermoelectrically cooled, optically immersed photovoltaic detector where the intensity was recorded with a National Instruments data acquisition system (DAQ). The pressure was measured using MKS 627D capacitance manometers with 100 and 200 Torr full scale pressure ranges and accuracies of 0.12%. The breath samples were collected in SKC 239 Series Exhaled Breath Sample Bags which have a volume of 1 L and are made of 4-ply low-background Flex Foil® PLUS material. The patient exhales into the bag through the exhaled breath fitting which is then closed. The breath sample is removed through the sample removal fitting and flows through the cell to be measured.

To implement the experimental WMS strategy, the laser was set to a fixed temperature and center current at the peak of the absorption, the current was then modulated with a high frequency, 10 kHz, sine wave. The WMS technique, although the laser is modulated across the absorption feature, only gives the value corresponding to the center wavelength. For this reason, an additional sinusoidal modulation with low frequency, 80 Hz, was added to the high frequency modulation so that the 2f/1f signal for a range of wavelengths could be determined. The purpose of this scan was to make sure the peak 2f/1f signal was measured. The resulting laser intensity, after having passed through the ammonia mixture in the multi-pass cell, was measured by the detector.

Figure 4:
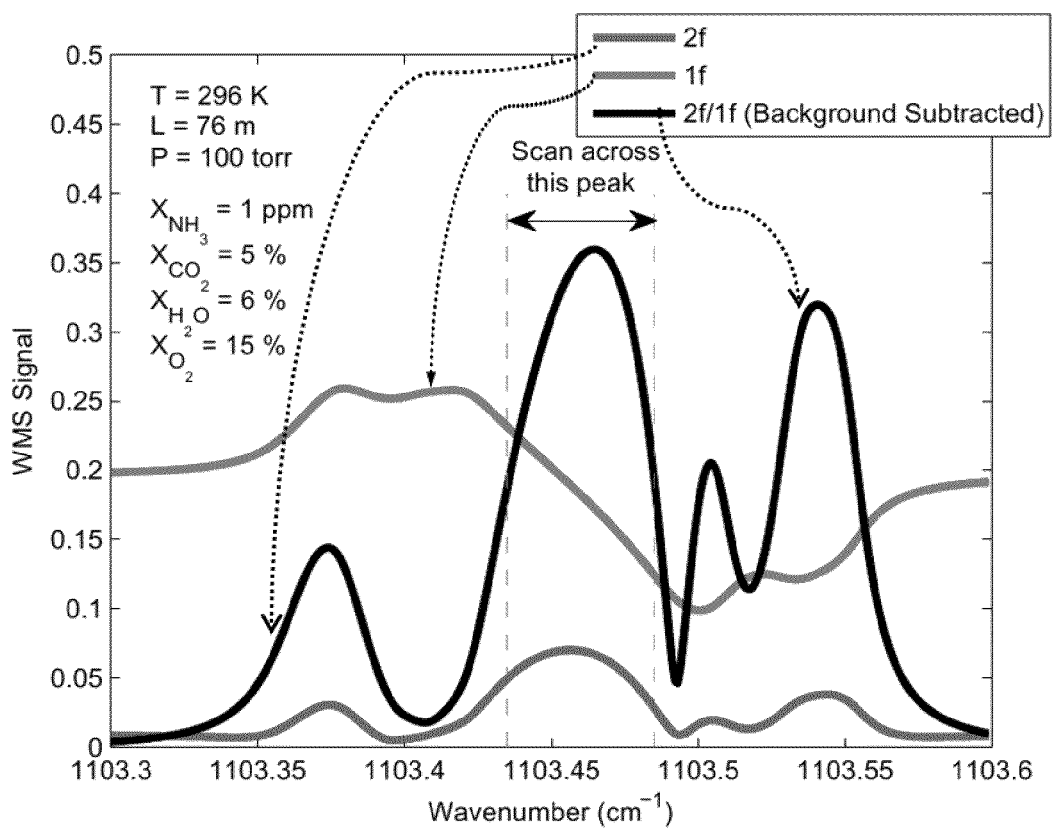
FIG. 4 depicts simulated WMS signals including the first and second harmonic signals as well as the background subtracted second harmonic normalized by first harmonic detection (2f/1f) signal showing the region of the slow scan.

Next, the recorded laser intensity with absorption was processed using a digital lock-in filter to determine the first and second harmonic components. The signal was then digitally filtered with a low pass Butterworth filter to remove the high frequency noise and isolate the desired harmonics. The actual signal of interest is the background subtracted 2f/1f signal. The experimental background signal was measured with pure nitrogen flowing through the cell, this signal was vectorially subtracted from the signal measured in the presence of the ammonia containing gas sample. This was calculated for eight slow scan cycles from which fifteen peak values could be determined. The peaks were found by taking the maximum value for each scan across the peak. These peaks were then averaged to determine the measured background subtracted WMS 2f/1f peak value, which could then be used to determine the ammonia mole fraction. FIG. 4 shows the output from the simulation for the first and second harmonic signals, the background subtracted 2f/1f signal, and the region of the peak that was scanned during the measurement.

Ammonia Equilibrium Test Under Different Conditions

Figure 5:
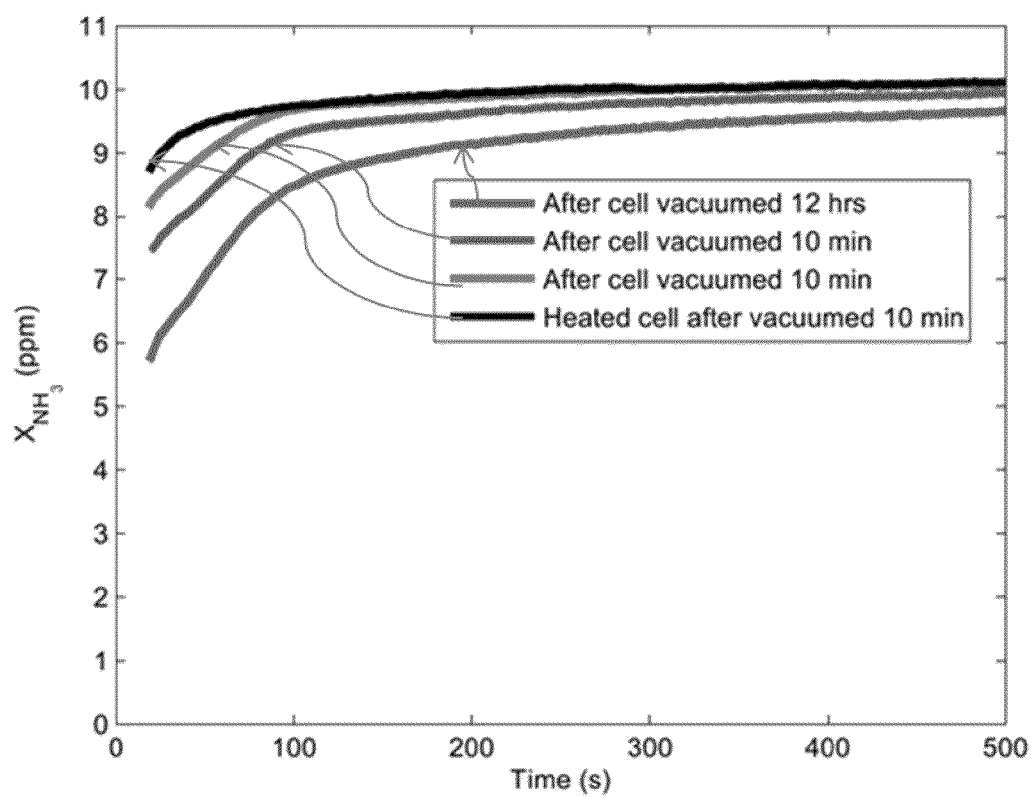
FIG. 5 depicts a comparison of equilibrium $X_{NH3}$ for clean, saturated, and heated cells.

Adsorption is an equilibrium process; the position of the equilibrium depends on three factors: the pressure, the temperature, and the stability of the molecule. These trends were verified for this sensor by measuring the ammonia mole fraction in the cell as an ammonia-nitrogen mixture flowed continuously through the cell. FIG. 5 compares equilibrium $X_{NH3}$ for clean, saturated, and heated cell. FIG. 5 shows the results for four different tests. The first test was performed after the cell was evacuated for 12 hours; since the cell was initially far from equilibrium, it approached the equilibrium slowly and the measured mole fraction continued to increase slowly, showing that it didn't reach equilibrium during the test time. The second and third tests were performed afterwards with 10 minutes of evacuating the cell. These approached the equilibrium faster as the cell started closer to equilibrium. The final test was performed with the cell heated to 35° C. The fast response was due to both the heating as well as being close to equilibrium initially due to the previous tests.

Figure 6:
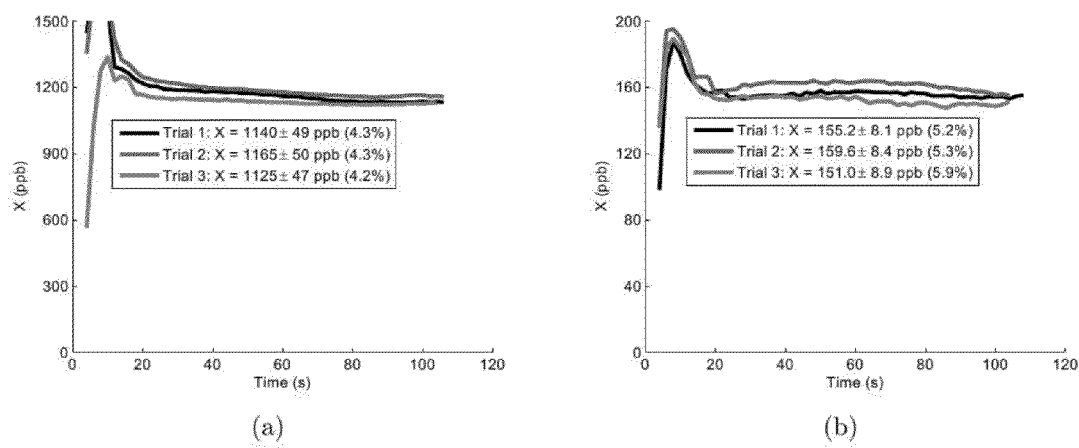
FIG. 6(a) depicts a continuous flow reaching equilibrium by measuring a gas mixture with ammonia levels near the high end.
FIG. 6(b) depicts a continuous flow reaching equilibrium by measuring a gas mixture with ammonia levels near the low end of the target range multiple times.

This verification was performed allowing a long time to reach equilibrium and using an ammonia-nitrogen mixture with a higher amount of ammonia than typical in breath. An additional test was therefore necessary with ammonia at typical amounts and with the limited volume allowed by the sample breath bag. The sample breath bag was filled with a pseudo breath mixture of ammonia, at a level in the upper range expected for breath, in nitrogen, oxygen, carbon dioxide, and water vapor and then flowed through the cell. This was repeated two more times and then another three times with a similar mixture for ammonia at a level in the lower range expected for breath. FIG. 6(*a*) depicts a continuous flow reaching equilibrium by measuring a gas mixture with ammonia levels near the high end, and FIG. 6(*b*) depicts a continuous flow reaching equilibrium by measuring a gas mixture with ammonia levels near the low end of the target range multiple times.

It can be seen in FIG. 6 that in both cases equilibrium was reached in the time provided by the limited volume of the bag and that the equilibrium value was repeatable within the measurement uncertainty. Ideal measurement conditions for flow from the breath sample bags were achieved using valves between the bag and the cell and between the cell and the vacuum pump to regulate the flow rate and pressure. The pressure increased to 100 torr in 40 seconds and then remained steady until the bag was empty, 70 seconds later. Since the bag volume is 1 liter, the flow rate was around 550 sccm (standard cubic centimeters per minute). This verification test showed that the flow rate and sample volume are adequate to reach the equilibrium flow conditions. The time required to reach the equilibrium in this case was shorter than in the previous calibration tests because the amount of ammonia was lower and, therefore, the disturbance from equilibrium was smaller.

The trend of the ammonia mole fraction was also different in this validation test compared to the previous one. The amount of ammonia in the cell first increases, then decreases as it approaches equilibrium rather than just increasing. The major difference between the ammonia-nitrogen mixture and the pseudo breath is that breath also contains water vapor. The significance of this is that water vapor is a molecule which also tends to adsorb. The water vapor adsorption reaction competes with the ammonia adsorption reaction. Initially, ammonia molecules are occupying the adsorption sites on the cell from previous tests, but when the water vapor molecules are present they can replace the ammonia disturbing the equilibrium and causing a net desorption of ammonia. Over time, with continuous flow, the equilibrium is re-established and the ammonia level still approaches the amount in the incoming sample.

WMS Simulation Sensitivity Analysis

Figure 7:
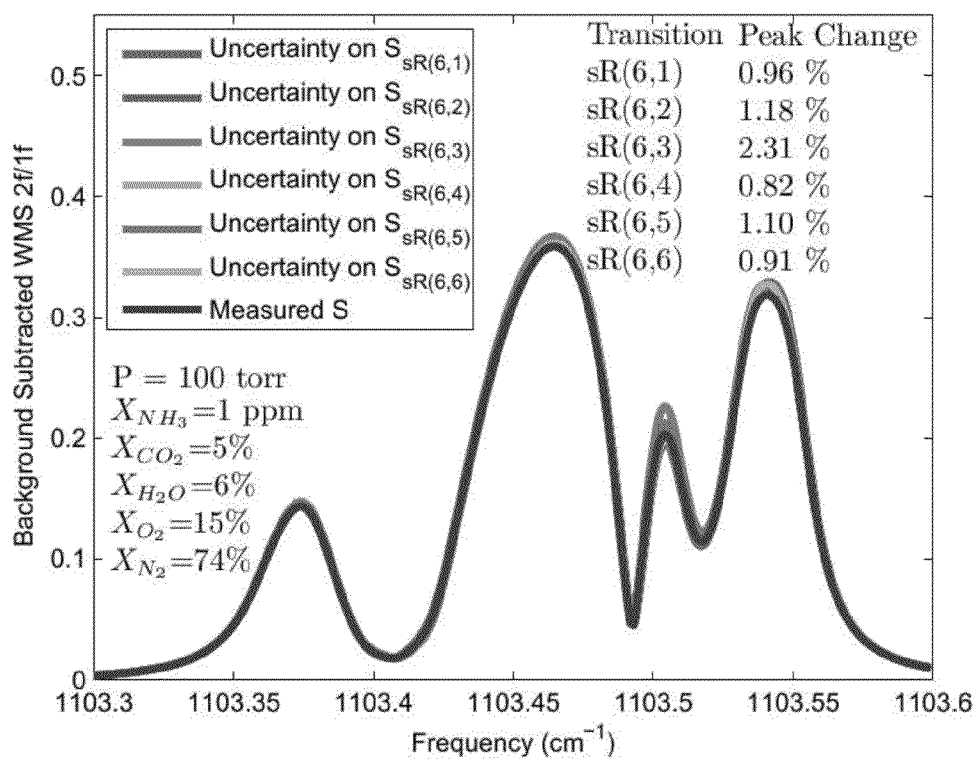
FIG. 7 depicts a comparison of simulated WMS 2f/1f peak for measured linestrengths to the simulation when each linestrength is changed by its uncertainty.

To infer the ammonia mole fraction, the measured peak signal was compared to the simulated peak. It was, therefore, necessary to quantify the sensitivity of the simulated peak value to the spectroscopic parameters, the gas properties, and the laser parameters. The linestrength and collisional broadening coefficients for ammonia in nitrogen, oxygen, carbon dioxide, and water vapor were measured. In order to determine the effect the uncertainty in these values had on the simulated signal, simulations were performed in which one of the parameters was adjusted by its uncertainty while the others were maintained at their measured value. The resulting peak value was compared to the peak value for the simulation with all of the parameters at their measured value. FIG. 7 compares simulated WMS 2f/1f peak for measured linestrengths to the simulation when each linestrength is changed by its uncertainty. FIG. 7 shows the effect of the uncertainty of the linestrength for each of the six ammonia transitions that make up the feature near $1103.46$ cm$^{-1}$. Transition sR(6,3) is the strongest and the main peak being measured so it has the largest resulting sensitivity leading to a change in the simulated peak of 2.31% with decreasing sensitivity as the transitions are further from transition sR(6,3).

The same analysis was used to study the effect of the uncertainty of the collisional broadening coefficients for each of the bath gases. The peak was most sensitive to nitrogen broadening, since it is the most abundant bath gas in breath, which led to a change in the simulated peak of 1.68%. Similar analysis was also done to determine the sensitivity of the peak to the gas properties and the laser parameters.

The relative concentrations of the other gases in breath were not simultaneously measured, since the interference only leads to a small uncertainty. Exhaled breath typically has 6% water vapor and between 3-6% carbon dioxide. The water vapor interference was negligible and the carbon dioxide interference was apparent for ammonia mole fractions less than 1 ppm. The interference was included in the simulation so the unknown effect was the relative difference in the interference due to variation in the carbon dioxide concentration. At a pressure of 100 torr and ammonia mole fraction of 200 ppb, the peak changed 1% for carbon dioxide concentrations between 3% and 6%. The uncertainty in the relative amounts of bath gases also affected the ammonia signal because they are included in the calculation of the collisional linewidth. Oxygen typically makes up 15% of breath while nitrogen accounts for the remainder. At a pressure of 100 torr, a change in the amount of water vapor by 1% resulted in a change in the peak value by 0.84%, while a change in the amount of carbon dioxide by 3% resulted in a change in the peak value by 0.62%, and a change in the amount of oxygen by 3% resulted in a change in the peak value by 0.43%. Since the nitrogen makes up the remainder of the mixture in the simulations, the effect of changing the amount of nitrogen was already accounted for.

The temperature of the gas in the cell was assumed to be room temperature which was measured occasionally and found to always be between 294 and 296 K. This 2 K difference led to a change in the simulated peak of 0.38%. The pressure in the cell during experiments was measured with an MKS manometer with a reported uncertainty of 0.12%. The mole fraction was measured after equilibrium flow conditions were achieved, during which there was a slight variation in the pressure. The total uncertainty in the measured pressure was 0.5% which led to a change in the simulated peak of 0.31%.

The manufacturer reported a cell path length of $76.45\pm0.05$ m which was confirmed within experimental error by measuring an ethylene absorption line. This uncertainty, due to uncertainty in the mirror radii of curvature, led to a change in the simulated peak of 0.07%.

The other inputs to the simulation were the laser parameters. As the temperature of the laser or center current was changed, the laser parameters changed as well. Also, for the same settings on different days, the laser parameters changed due to minor changes in the laser temperature within the setting. The day to day changes led to peak differences between 2-3%, so the laser parameters were measured before the sensor was used each day. The laser parameters were measured while the laser was being modulated with the high frequency sinusoid, but without the slow scan. There was some variation in the laser parameters at different center currents, which is equivalent to the variation as the laser is scanned across the peak. It was important, therefore, to record the laser parameters for the laser settings corresponding to the peak, which was used to compare the measurement to the simulation. Since there was some uncertainty in the exact peak location it was important to quantify the sensitivity of the peak to the laser parameters at different center currents near the peak. Based on measurements without the scan, the peak was consistently within a variation of 0.3 mA in the center current. Simulations using laser parameters in this range led to peak differences of 0.8%. There was also some uncertainty in the laser parameters based on the analysis technique used to measure them. This was investigated by determining the laser parameters multiple times for the exact same laser settings over time. The resulting variation in the laser parameters led to peak differences between 0.6-0.8%. It is likely that the variation in the laser parameters at the different center current settings was due to measurement error rather than the small change in laser settings. Therefore, by measuring the laser parameters before using the sensor, the simulation had a sensitivity to the measured laser parameters of 0.8%.

Figure 8:
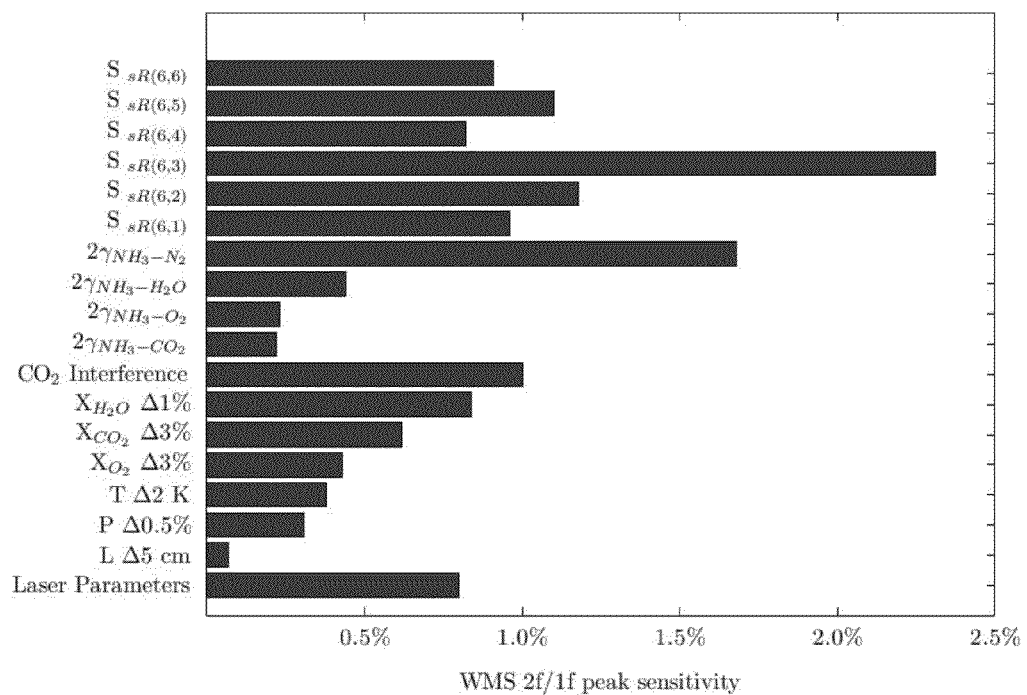
FIG. 8 depicts the effect of the input parameters' uncertainty on the simulated WMS 2f/1f peak.

FIG. 8 depicts the effect of the input parameters' uncertainty on the simulated WMS 2f/1f peak. Sensitivity analysis, shown in, FIG. 8, shows that the most significant input parameters to the simulation program were the linestrength of transition sR(6,3) and the collisional broadening coefficients for ammonia in nitrogen. Based on this analysis, the uncertainty in the simulated peak value was found by combining the effects of the uncertainties in the inputs using the Euclidean norm. For ammonia mole fractions less than 1 ppm, when the effect of the carbon dioxide interference was included, the uncertainty in the simulated peak was found to be 4.05%. For levels above 1 ppm, the uncertainty was found to be 3.92%. Since the measured mole fraction is proportional to the simulated peak, the uncertainty in the peak can be directly applied to uncertainty in the measured mole fraction.

The uncertainty measurement can take into account statistical uncertainty as well as uncertainty in all the inputs, such as interference, spectroscopic parameters, laser parameters, path length, pressure, and so on.

Detectability Limit

Figure 9:
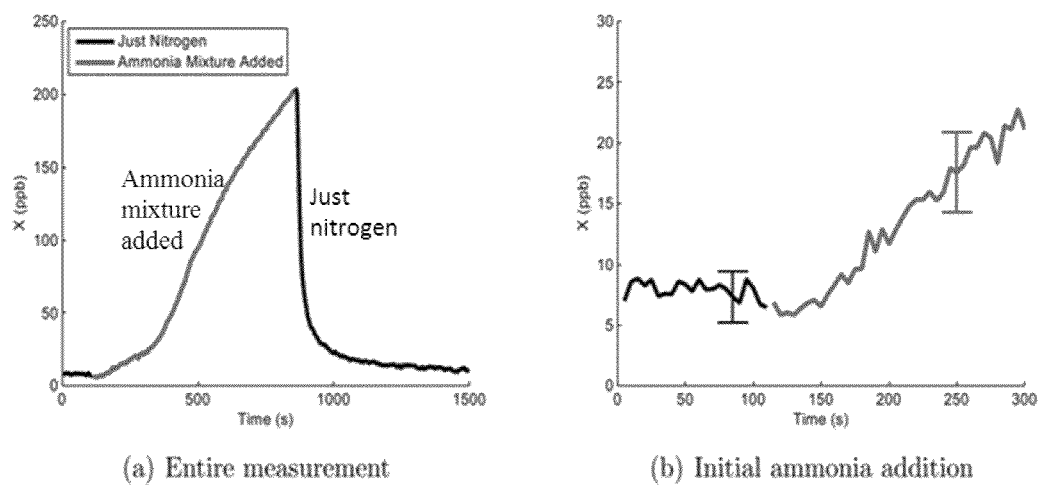
FIG. 9 depicts the sensor measurement of low levels of ammonia using WMS.

To quantify the sensor's detectability limit and sensitivity, an experiment was performed in which the ammonia mole fraction was measured as a small amount of ammonia was added to nitrogen flowing through the cell at 1 liter per minute. FIG. 9a shows the results for this experiment. Initially pure nitrogen was measured, then a 9 ppm ammonia in nitrogen mixture was added at a slowly increasing fractional flow rate, then the ammonia mixture was turned off so that just nitrogen flowed through the cell. It can be seen that the measured amount of ammonia slowly increased as more ammonia was added to the flow and then quickly decreases to a small amount of residual ammonia as the cell was flushed with nitrogen. FIG. 9b shows a more detailed analysis of the measurements as ammonia was first added.

Figure 10:
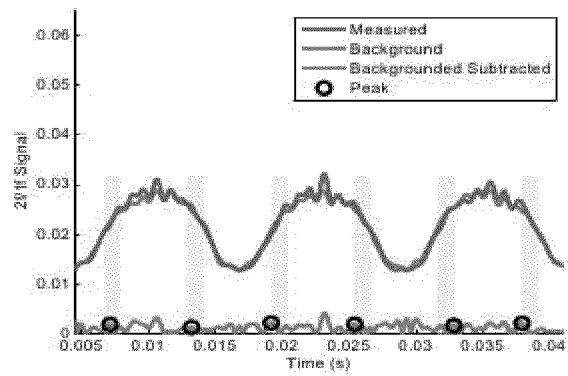
FIG. 10(a) depicts WMS 2f/1f results for (a) pure N2.
FIG. 10(b) depicts WMS 2f/1f results after the initial addition of ammonia.
FIG. 10(c) depicts WMS 2f/1f results once the amount of ammonia reached typical levels in breath.
Figure 10:
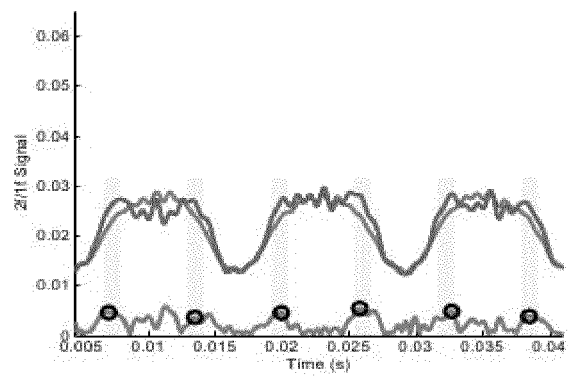
Figure 10:
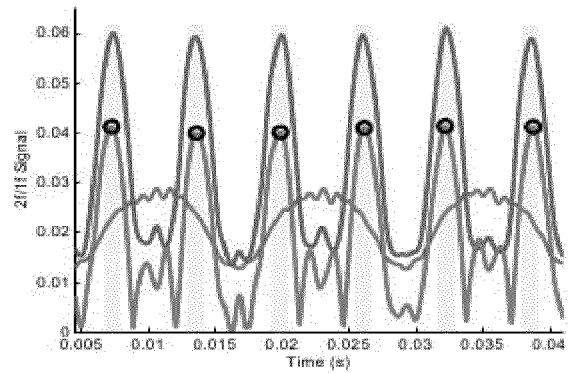

The sensor measured an ammonia concentration of less than 10 ppb when pure nitrogen was in the cell; this erroneous measurement was due to fluctuations in the background signal. The background signal used for this experiment was the average of 10 measurements with pure nitrogen flowing through the cell. FIG. 10(a) depicts WMS 2f/1f results for (a) pure N2; FIG. 10(b) depicts WMS 2f/1f results after the initial addition of ammonia; and FIG. 10(c) depicts WMS 2f/1f results once the amount of ammonia reached typical levels in breath. FIG. 10a shows how the measurement of pure nitrogen gives a non-zero peak value after background subtraction. Some erroneous peaks were ignored by only recording the maximum value from each of the peak regions, shown as the shaded region. For a detectability limit defined when the ratio of measured peak to background peak is greater than one, the detectability limit of the sensor is 10 ppb. This is essentially when the signal to noise ratio is greater than 1.

After the addition of the ammonia mixture, peaks began to become distinct from the background signal, as seen in FIG. 10b. The peak value used to determine the ammonia mole fraction was the average of fifteen peaks, note that fewer are shown for clarity. The measurement uncertainty was defined as the standard deviation in these fifteen peak values. The uncertainty in the peak value at a measured ammonia mole fraction of 18.3 ppb was 18.2%. Combining this uncertainty with the uncertainty in the simulated peak using the euclidean norm led to a total uncertainty of 18.6% or 3.4 ppb.

Since this sensor was designed to measure the amount of ammonia in exhaled breath it was important to quantify the sensitivity near expected values in breath. Healthy patients are expected to have anywhere from 100 to 500 ppb ammonia, while patients with CKD are expected to have greater than 1 ppm ammonia. FIG. 10c shows the signal for a measurement of 154.6 ppb, in the lower ammonia range required to be measured. In this case, the peaks are clearly distinguished from the background level. The measurement uncertainty was found to be 2.1% leading to a total uncertainty of 4.58% or 7.1 ppb.

Real Time Measurement of Breath Samples from Healthy Patients

Figure 11:
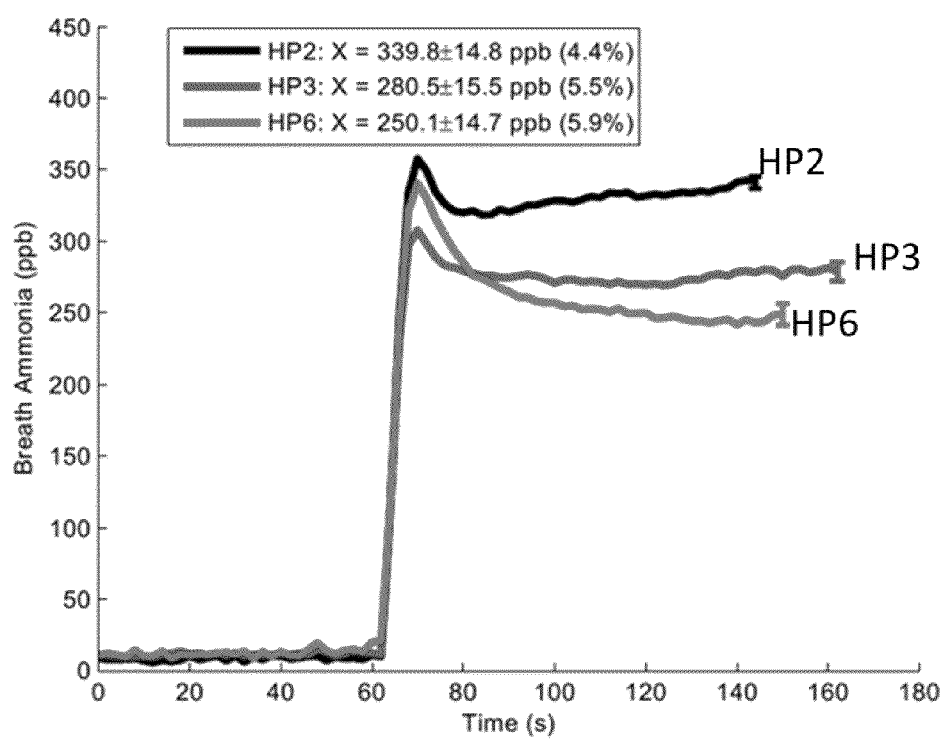
FIG. 11 depicts the measurement of breath samples from three healthy patients after 1 minute of nitrogen flow from the sample bag.

The sensor was implemented to study the ammonia in the exhaled breath of healthy individuals. Measurements were taken in real time with the breath sample bag as a buffer volume. The cell was evacuated and then opened to the sample bag which was initially filled with nitrogen. The initial nitrogen flow provided time for the pressure in the cell to increase and reach constant flow conditions as well as being a verification of the zero background. When the bag was empty, the healthy patient exhaled into the sample bag through the exhaled breath fitting and then closed it. Immediately, the breath flowed into the cell through the sample removal fitting. FIG. 11 shows three examples of the measurement of breath samples from different healthy patients. The first 60 seconds show the measurement when only nitrogen was in the bag, after which the patient exhaled into the bag and the sensor measured the ammonia in the breath. Previous experiments were done to verify that the flow rate was sufficiently high so that the gas in the cell does not mix, but is completely replaced by the incoming sample. Therefore, the initial rise in mole fraction is over the time it takes for the breath sample to completely fill the cell and for the nitrogen to be removed. After this, the flow continues as equilibrium is established until the bag is empty.

Figure 12:
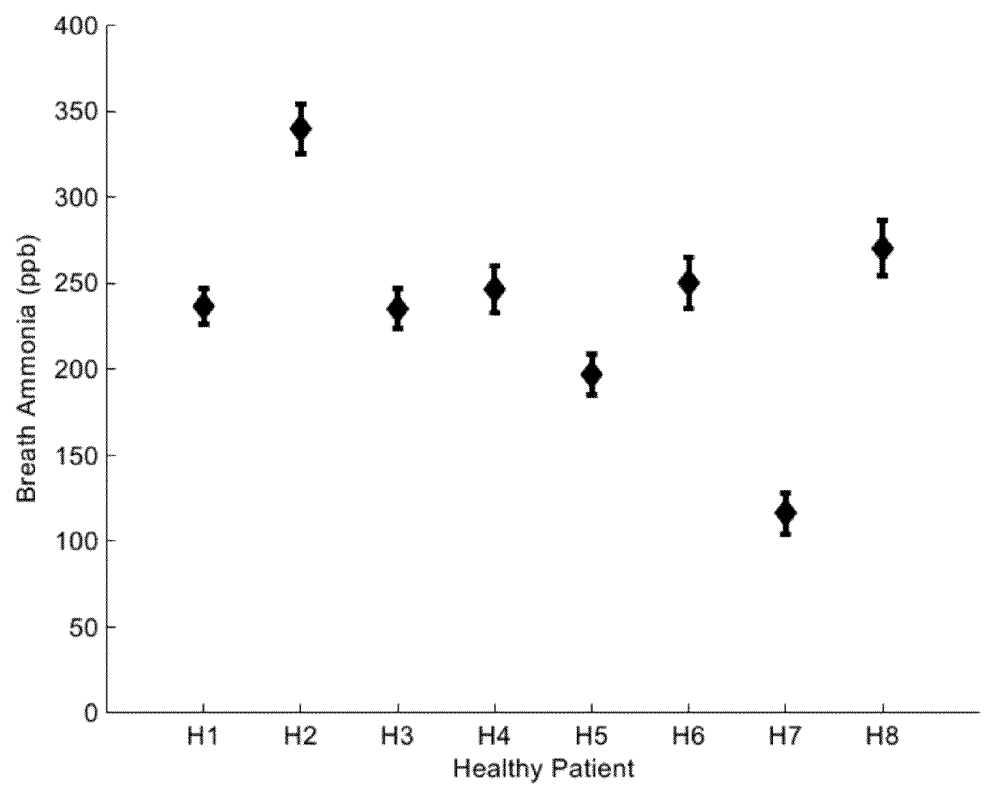
FIG. 12 depicts the results from eight healthy patients including male and female, smokers and non-smokers, between the ages of 18 and 50.

The amount of ammonia in the exhaled breath of eight different healthy patients was measured. The reported ammonia level for the measurement is the average measured value for the last five measurements, taken over the last ten seconds before the sample was consumed. The reported uncertainty combines the uncertainty from the standard deviation in these five measurements, the measurement uncertainty which comes from the standard deviation in WMS 2f/1f peak height over 15 scanned peaks, and the simulation uncertainty based on the uncertainties of the input parameters. FIG. 12 shows the results for these eight patients, all of which were between 100 and 350 ppb, within the expected range for healthy patients. The eight healthy patients include male and female, smokers and non-smokers, between the ages of 18 and 50.

Figure 13:
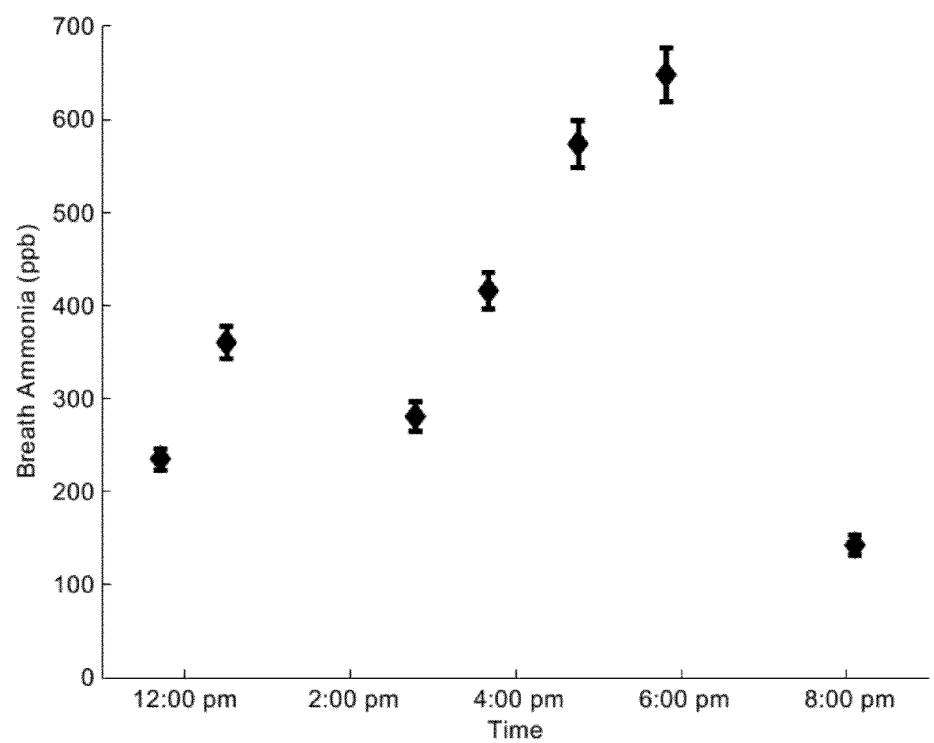
FIG. 13 depicts results for one healthy patient throughout the day where the lunch meal was at 1:30 pm and the dinner meal was at 7:00 pm.

The amount of ammonia in the exhaled breath of one healthy patient over the course of the afternoon was also measured. FIG. 13 depicts results for one healthy patient throughout the day where the lunch meal was at 1:30 pm and the dinner meal was at 7:00 pm. FIG. 13 shows that the amount of ammonia decreased after a meal, then increased steadily between meals, and again decreased after another meal. This is in agreement with results from previous work. See, for example, Manne, J., et al., *Applied Optics* 2006, 45, 9230-9237, which is incorporated by reference in its entirety. The amount of ammonia was within the expected range except long after one meal before the next when it was above 500 ppb.

Measurement of Breath Samples from Patients Diagnosed with Chronic Kidney Disease Breath samples were collected from patients diagnosed with CKD in the exhaled breath sample bags and transported to the research facility. These bags are specifically designed for collecting and storing human breath samples. A study was done previously to investigate the suitability of the bag material for storing atmospheric samples containing ammonia for short periods of time. The results were that 100% of the ammonia was recovered after 2 hours and over 90% of the ammonia was recovered after 6 hours. See, for example, Akdeniz, A., et al., *Transactions of the ASABE* 2011, 54, 653-661, which is incorporated by reference in its entirety. The study also recommended a procedure for cleaning the bags to make them suitable for reuse. The cleaning procedure involved emptying the bag, flushing it with room air, filling it with zero air for 24 hours, emptying it, then refilling it with zero air again to measure the residual gas concentrations. Following this procedure the bags were found to have less than 25 ppb residual ammonia. Another study investigating the bags for breath research included heating to 45° C. as part of the cleaning procedure. See, for example, Mochalski, P., et al., *Journal of Chromatography B-Analytical Technologies in the Biomedical and Life Sciences* 2009, 877, 189-196, which is incorporated by reference in its entirety.

To verify that the bags were suitable for storing the breath samples, an experiment was designed to measure the amount of ammonia in the bag over time. Since the full volume of the bag was required for each measurement, three bags were filled with the same pseudo-breath mixture at the same time. The amount of ammonia in consecutive bags was measured immediately, after 2½ hours, and after 3½ hours. This experiment was performed for two different initial ammonia mole fractions. The results, listed in Table 2, show that a substantial portion of the ammonia was lost over time. These losses are likely due to the ammonia molecules adsorbing to surfaces of the sample bag. The different behavior between these conditions and the ones in the previous research investigating the bags is likely due to the condensation of water, which has higher partial pressures in breath than in the atmosphere.

TABLE 2

Percent remaining at 2½ and 3½ hours for each of the initial mixtures.

| $X(t)/X_{initial}$ | $X_{initial}$ = 558 ppb | $X_{initial}$ = 1073 ppb |
|---|---|---|
| t = 2½ hours | 46% | 44% |
| t = 2½ hours | 37% | 36% |

Figure 14:
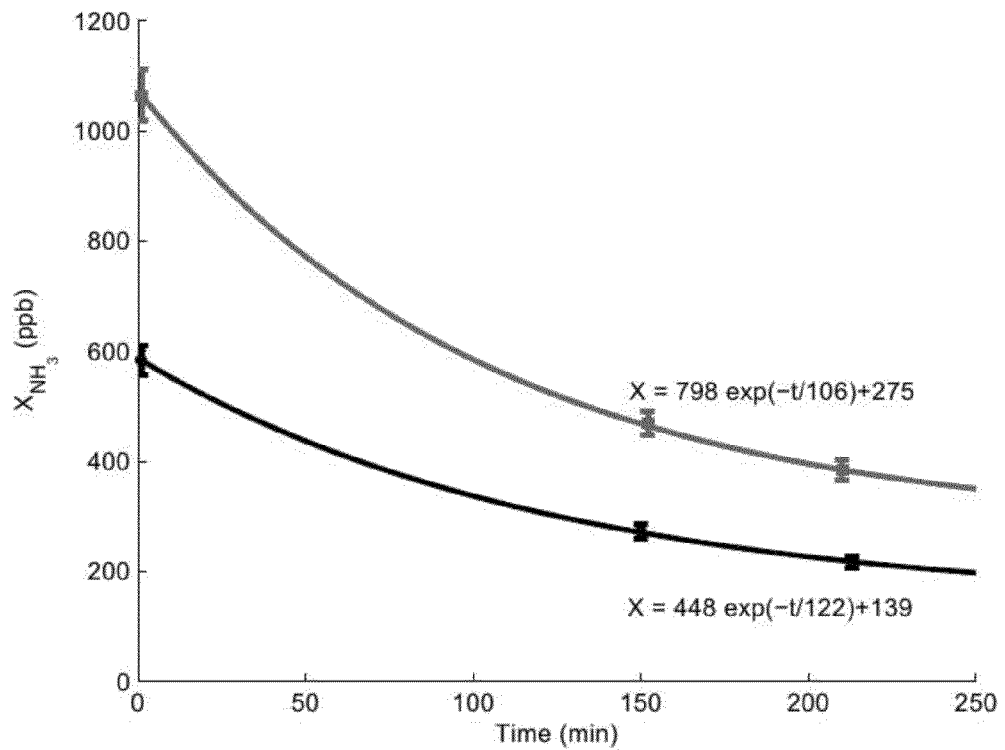
FIG. 14 depicts measurements of two different mixtures each added to three new sample bags at the same time then measured initially, after 2½ hours, and after 3½ hours, which was used to develop a correlation to correct for the loss of ammonia to the bag.

The results from the verification experiment were used to develop a correlation which was used to calculate the initial amount of ammonia in the breath sample based on the measured amount and the time between the sample acquisition and the measurement. FIG. 14 depicts measurements of two different mixtures each added to three new sample bags at the same time then measured initially, after 2½ hours, and after 3½ hours, which was used to develop a correlation to correct for the loss of ammonia to the bag.

FIG. 14 shows the results of each experiment fit with an exponential decay correlation. According to the Langmuir Isotherm, at low concentrations of ammonia, the equilibrium amount of ammonia in the gas phase is linearly proportional to the initial amount of ammonia in the gas phase. Since the time constants for the decays were similar, the average value was used in the final correlation along with iteration to determine the equilibrium value. The correlation was then used to determine the initial amount of ammonia in the breath sample based on the amount measured at a recorded time after the sample was collected.

Figure 15:
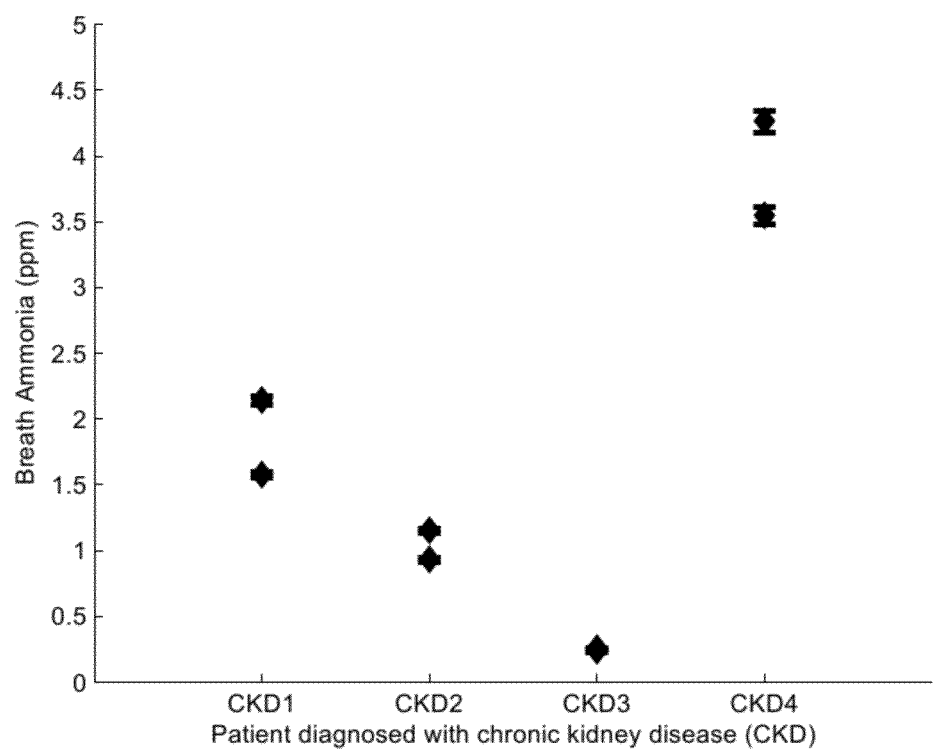
FIG. 15 depicts breath ammonia results from four patients diagnosed with chronic kidney disease (CKD).

Since the breath samples were not immediately measured, the procedure involving initially filling the bags with nitrogen was not used. Instead, the cell was evacuated before the breath sample flowed through the cell. It took longer to reach the steady flow condition, but equilibrium was still reached before the sample was depleted. Two samples from four different patients were collected and analyzed. FIG. 15 depicts breath ammonia results from four patients diagnosed with CKD and shows that each of the patients had significantly different amounts of ammonia in their breath. Patients CKD1, 2, and 4 had levels in the expected range for patients diagnosed with CKD, while patient CKD3 had levels in same range as expected for healthy patients.

Patients are diagnosed with CKD when their kidneys do not properly filter their blood, resulting in the accumulation of toxins in their blood, one of which is urea. Ammonia is part of the urea cycle and will therefore likewise accumulate in the blood. Ammonia can diffuse out of the blood into the lungs when the ammonia levels become higher than the ammonia levels in the air. See, for example, Timmer, B., et al., *Sensors and Actuators B-Chemical* 2005, 107, 666-677, which is incorporated by reference in its entirety. The relationship between breath ammonia and blood urea makes an ammonia breath sensor a potential diagnostic and monitoring tool for CKD. Patients with CKD are treated by dialysis, during which their blood is filtered. As a result of the filtering, the urea in the blood decreases during dialysis. The adequecy of dialysis is measured with the Urea Reduction Ratio (URR) which is the percent decrease in Blood Urea Nitrogen (BUN).

$$URR = \left(\frac{BUN_{Before\ Dialysis} - BUN_{After\ Dialysis}}{BUN_{Before\ Dialysis}}\right) \cdot 100\%$$

To compare the relationship between breath ammonia and blood urea a Breath Ammonia Reduction Ratio (BARR) can be calculated to determine the percent decrease in breath ammonia.

$$BARR = \left(\frac{X_{Before\ Dialysis} - X_{After\ Dialysis}}{X_{Before\ Dialysis}}\right) \cdot 100\%$$

Figure 16:
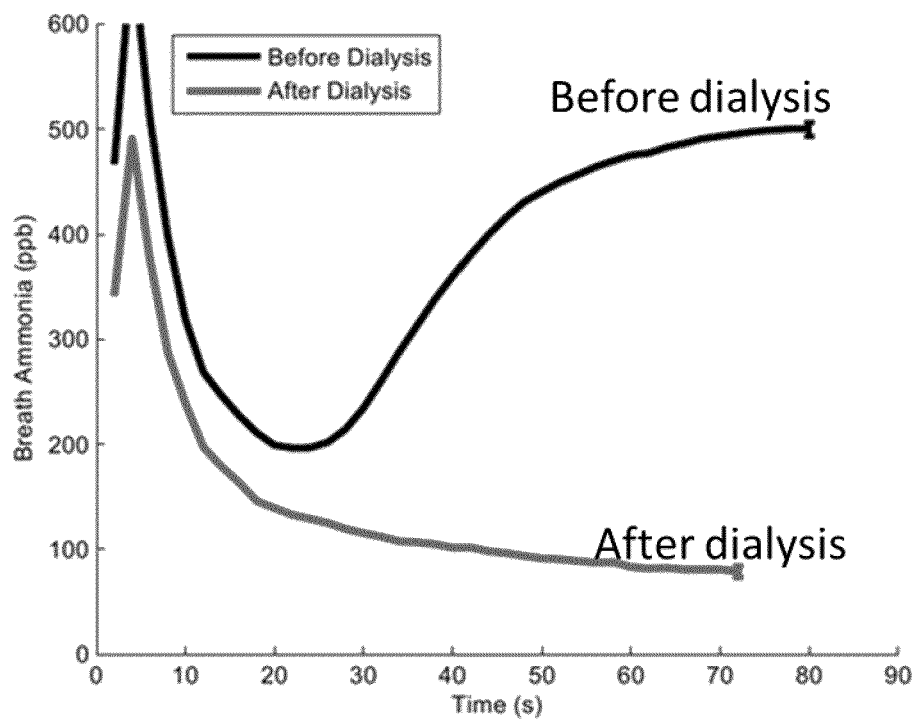
FIG. 16 depicts measurement of the breath ammonia for patient CKD2 from samples taken before and after undergoing dialysis treatment.
Figure 17:
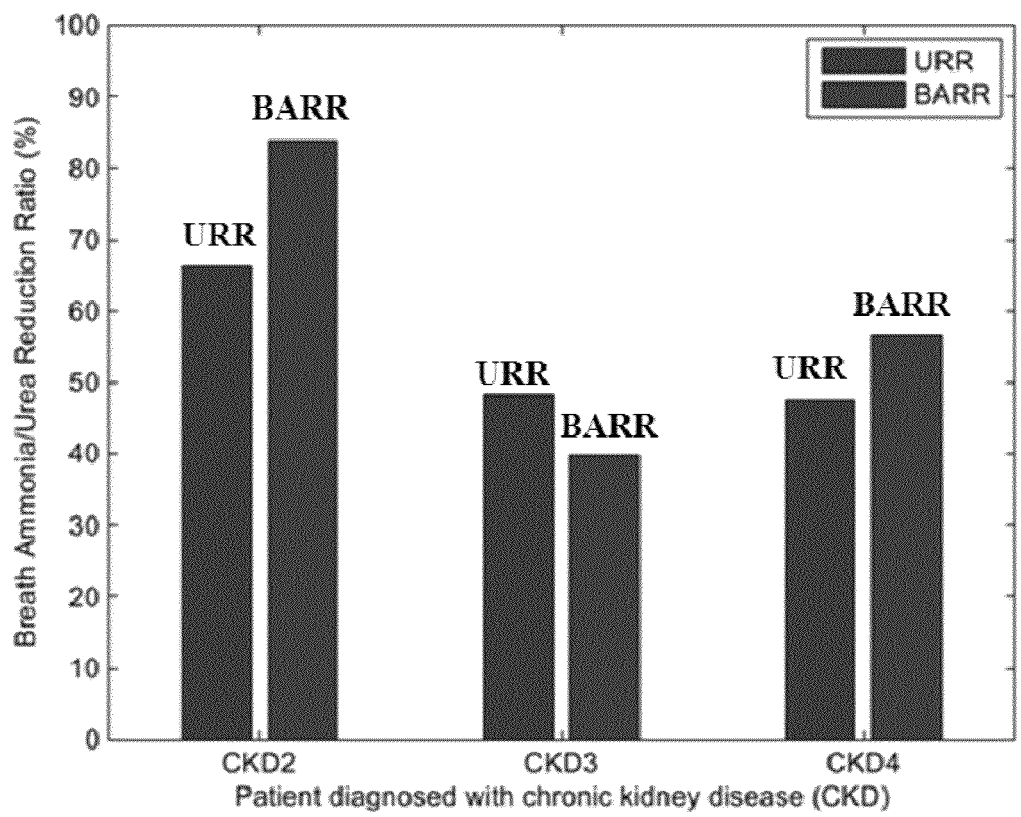
FIG. 17 depicts comparison between the Urea Reduction Ratio (URR) and Breath Ammonia Reduction Ratio (BARR), used to test the adequacy of the dialysis treatment, for three patients diagnosed with CKD.

FIG. 16 shows the measurements of the breath ammonia from patient CKD2 taken before and after the dialysis treatment. Blood tests were performed for patients CKD2, 3 and 4, so a comparison between the URR and BARR was made. For each patient a decrease in the BUN was accompanied by a decrease in the breath ammonia level. FIG. 17. shows the comparison between the URR and the BARR for patients CKD2, 3, and 4. Dialysis is considered successful when the URR is greater than 65%. See, for example, Narasimhan, L. R., et al., *Proceedings of the National Academy of Sciences of the United States of America* 2001, 98, 4617-4621, which is incorporated by reference in its entirety. While the BARR and URR are not the same, they do give the same qualitative measure of adequacy.

This sensor can be portable, and can be a diagnostic and monitoring tool. Additional measurements studying more patients with specific guidelines about meals can help draw conclusions about the quantitative relationship between CKD and breath ammonia.

Other embodiments are within the scope of the following claims.

What is claimed is:

1. A method of detecting the amount of ammonia in a sample comprising:
   flowing a gas including ammonia from a subject through a multi-pass absorption cell;
   passing a laser beam through the gas in the multi-pass absorption cell;
   detecting the intensity of the laser beam after the laser beam passes through the gas in the multi-pass absorption cell;
   recording the intensity of the laser beam after the intensity of the laser beam is detected; and
   processing the recorded intensity of the laser beam to determine a first harmonic component and a second harmonic component and the amount of ammonia in the sample, processing including adding a low frequency modulation to a high frequency modulation to determine a second harmonic normalized by a first harmonic for a range of wavelengths, and determining an ammonia mole fraction using a background subtracted second harmonic normalized by the first harmonic.

2. The method of claim 1, further comprising flowing the gas continuously.

3. The method of claim 1, further comprising filtering the laser beam intensity with a filter to remove high frequency noise and to isolate the first and the second harmonics.

4. The method of claim 1, further comprising normalizing the second harmonic by the first harmonic.

5. The method of claim 1, further comprising determining peak of the second harmonic normalized by the first harmonic.

6. The method of claim 1, further comprising measuring a background signal.

7. The method of claim 1, further comprising subtracting the background signal from the second harmonic normalized by the first harmonic.

8. The method of claim 1, wherein the ammonia mole fraction is determined using Beer's Law.

9. The method of claim 1, further comprising pretreating the multi-pass absorption cell with the gas.

10. The method of claim 1, wherein the amount of ammonia is detected to diagnose or monitor chronic kidney disease.

11. The method of claim 1, wherein the amount of ammonia is detected during dialysis.

12. The method of claim 1, wherein the amount of ammonia is detected to diagnose or monitor *helicobacter pylori* infection.

13. The method of claim 1, wherein the amount of ammonia is detected to diagnose or monitor encephalopathy.

14. The method of claim 1, wherein the amount of ammonia is detected to diagnose or monitor chronic liver disease.

15. A method of diagnosing or monitoring chronic kidney disease comprising:
- flowing a gas including ammonia from a subject through a multi-pass absorption cell;
- passing a laser beam through the gas in the multi-pass absorption cell;
- detecting the intensity of the laser beam after the laser beam passes through the gas in the multi-pass absorption cell;
- recording the intensity of the laser beam after the intensity of the laser beam is detected; and
- processing the recorded intensity of the laser beam to determine a first harmonic component and a second harmonic component and the amount of ammonia in the sample, processing including adding a low frequency modulation to a high frequency modulation to determine a second harmonic normalized by a first harmonic for a range of wavelengths; and
- determining an ammonia mole fraction using a background subtracted second harmonic normalized by the first harmonic.

16. A sensor for detecting ammonia comprising:
- a sample reservoir configured to contain a gas including ammonia from a subject;
- a first controller configured to adjust pressure and flow rate of the gas from the sample reservoir into a first conduit;
- a multi-pass absorption cell fluidly connected to the first conduit and configured to contain a portion of the gas from the sample reservoir;
- a laser source configured to pass a laser beam through the gas in the multi-pass absorption cell;
- a detector configured to measure the intensity of the laser beam; and
- an analyzer configured to provide a concentration of ammonia in the gas by adding a low frequency modulation to a high frequency modulation to determine a second harmonic normalized by a first harmonic for a range of wavelengths and determining an ammonia mole fraction using a background subtracted second harmonic normalized by the first harmonic.

17. The sensor of claim 16, wherein the sensor further comprises a cooling system configured to cool the laser source.

18. The sensor of claim 16, wherein the sensor further comprises collimation optics between the laser source and the multi-pass absorption cell.

19. The sensor of claim 16, wherein the sensor further comprises a recorder configured to record the laser beam intensity after the laser beam passes through the gas in the multi-pass absorption cell.

20. The sensor of claim 16, wherein the sensor further comprises a first pressure measuring instrument configured to measure the pressure of the gas, wherein the pressure measuring instrument is between the sample reservoir and the multi-pass absorption cell.

21. The sensor of claim 16, wherein the sensor is calibration free.

22. The sensor of claim 16, wherein the sample reservoir includes breath sample.

23. The sensor of claim 16, wherein the first controller is configured to keep the pressure substantially constant.

24. The sensor of claim 16, wherein the laser source includes a quantum cascade laser.

25. The sensor of claim 16, wherein the laser source is tunable over 1100.4 to 1108.2 $cm^{-1}$.

26. The sensor of claim 16, wherein the laser source is configured to operate near 1103.46 $cm^{-1}$.

27. The sensor of claim 16, wherein the multi-pass cell further comprises a gas outlet connecting to a second controller configured to adjust pressure and flow rate of the gas from the multi-pass absorption cell into a second conduit.

28. The sensor of claim 27, wherein the second controller is configured to connect to a vacuum pump through the second conduit.

29. The sensor of claim 28, wherein the sensor further comprises a second pressure measuring instrument configured to measure the pressure of the gas, wherein the pressure measuring instrument is between the gas outlet and the vacuum pump.

30. The sensor of claim 16, wherein the pressure of the multi-pass cell is less than 200 Torr.

31. The sensor of claim 16, wherein the ammonia detected is between 10 parts-per-billion to 5 parts-per-million.

32. The sensor of claim 16, wherein the sensor is portable.

33. The sensor of claim 16, wherein the uncertainty of the sensor is less than 10%.

34. The sensor of claim 16, wherein the uncertainty of the sensor is less than 7%.

35. The sensor of claim 16, wherein the uncertainty of the sensor is less than 5%.

36. The sensor of claim 33, wherein the uncertainty of the sensor takes into account interference, spectroscopic parameters, laser parameters, path length, and pressure.

\* \* \* \* \*